United States Patent [19]

Sounik et al.

[11] Patent Number: 5,498,804
[45] Date of Patent: Mar. 12, 1996

[54] PROCESS FOR PREPARING 4-HYDROXYPHENYLMETHYLCARBINOL

[75] Inventors: James R. Sounik; Graham N. Mott; Charles B. Hilton, all of Corpus Christi, Tex.

[73] Assignee: Hoechst Celanese Corporation, Sommerville, N.J.

[21] Appl. No.: 406,266

[22] Filed: Mar. 17, 1995

[51] Int. Cl.⁶ .................................................. C07C 39/10
[52] U.S. Cl. .................................................. 568/764
[58] Field of Search ...................................... 568/764

[56] References Cited

U.S. PATENT DOCUMENTS

| | | | |
|---|---|---|---|
| 4,032,513 | 6/1977 | Fujiwara et al. | 260/47 |
| 4,544,704 | 10/1985 | Hefner, Jr. | 525/108 |
| 4,678,843 | 7/1987 | Elmore et al. | 525/378 |
| 4,912,173 | 3/1990 | Keene et al. | 525/378 |
| 4,962,147 | 10/1990 | Vicari | 524/460 |
| 4,965,400 | 10/1990 | Vicari | 560/130 |
| 5,041,614 | 8/1991 | Aslam et al. | 560/130 |
| 5,084,533 | 1/1992 | Shah et al. | 526/75 |
| 5,087,772 | 2/1992 | Shah et al. | 568/804 |
| 5,151,546 | 9/1992 | Shah et al. | 560/130 |
| 5,247,124 | 9/1992 | Aslam et al. | 560/130 |

*Primary Examiner*—Werren B. Lone
*Attorney, Agent, or Firm*—James J. Mullen; Donald R. Cassady

[57] ABSTRACT

The present invention provides a unique and novel way of producing carbinols such as 4-hydroxyphenylmethylcarbinol (HPMC). In this new process, a ketone such as 4-hydroxyacetophenone (4-HAP) is heated under suitable hydrogenation conditions of temperature and pressure in the presence of a suitable catalyst and for a sufficient period of time to form HPMC.

12 Claims, No Drawings

PROCESS FOR PREPARING 4-HYDROXYPHENYLMETHYLCARBINOL

BACKGROUND OF THE INVENTION

1. Field of the Invention

The present invention relates to a process for the production of 4-hydroxyphenylmethylcarbinol (HPMC) [sometimes referred to as 1-(4-hydroxyphenyl)ethanol-(1,4-HPE)] by the hydrogenation of 4-hydroxyacetophenone (4-HAP).

2. Description of the Prior Art

It is known in the art to produce 4-hydroxystyrene (HSM) and derivatives thereof such as poly(4-hydroxystyrene) (PHS), which have applications in the production of adhesives, coating compositions, photoresists, and the like. In the PHS area, there is a need to produce such material in the least amount of process steps in order to provide efficiency. The prior art has utilized a five-step process in order to produce PHS. We have now found that PHS can be produced in three steps or less.

The following prior art references are disclosed in accordance with the terms of 37 CFR 1.56, 1.97, and 1.93.

U.S. Pat. No. 5,087,772 (issued Feb. 11, 1992) discloses the preparation of HSM by reacting 4-acetoxystyrene (ASM) with a suitable alcohol in the presence of a catalytic amount of a suitable base.

European Patent Application No. 0-128-984 (publication no.), filed Aug. 30, 1983, discloses a process for the production of para-vinyl phenol (HSM) by dehydrogenation of para-ethyl phenol.

European Patent Application No. 0-108-624 (publication no.), filed Nov. 4, 1983, discloses a process for the production of p-vinyl phenol polymer (polyhydroxystyrene polymer-PHS) by polymerizing p-vinyl phenol (HSM) in the presence of water and iron.

U.S. Pat. No. 4,032,513 (issued Jun. 28, 1977) discloses a process of producing PHS by cationically polymerizing HSM in the presence of a nitrile, such as $CH_3CN$, using a cationic polymerization initiator in a homogeneous reaction system.

U.S. Pat. No. 5,041,614 discloses a method for the preparation of 4-acetoxystyrene (ASM) from 4-acetoxyphenylmethylcarbinol. (Note Formula I for the structural formula for ASM).

U.S. Pat. No. 5,084,533 discloses a process for the neat hydrogenation of 4-acetoxyacetophenone in the production of 4-acetoxystyrene (ASM).

U.S. Pat. No. 5,151,546 discloses a process for preparing 4-acetoxystyrene (ASM) by heating 4-acetoxyphenylmethylcarbinol with an acid catalyst.

U.S. Pat. No. 5,245,074 discloses a process for preparing 4-acetoxystyrene (ASM) through the 4-acetoxyacetophenone/4-acetoxyphenylmethylcarbinol route.

U.S. Pat. No. 5,247,124 discloses a process for preparing substituted styrenes such as ASM by reacting a bisarylalkyl ether in the presence of an acid catalyst. *J. Org. Chem.*, (1954), 19, 1205, discloses the use of copper chromite catalysts in the hydrogenation of ketones.

Other prior art references which relate to the present invention include U.S. Pat. Nos. 2,276,138; 3,547,858; 4,544,704; 4,678,843; 4,689,371; 4,822,862; 4,857,601; 4,868,256; 4,877,843; 4,898,916; 4,912,173; 4,962,147; and U.S. Pat. No. 4,965,400.

All of the above-cited prior art and any other references mentioned herein are incorporated herein by reference in their entirety.

SUMMARY OF THE INVENTION

The present invention provides a unique and novel way of producing 4-hydroxyphenylmethylcarbinol (HPMC). In this new process, 4-hydroxyacetophenone (4-HAP) is heated under suitable hydrogenation conditions of temperature and pressure in the presence of a suitable palladium catalyst and for a sufficient period of time to form the HPMC. Subsequently, HPMC can be dehydrated and polymerized to form PHS.

DETAILED DESCRIPTION OF THE INVENTION

In the overall scheme of preparing PHS in a limited number of process steps, it has been unexpectedly found that the intermediate product, i.e. 4-hydroxymethylcarbinol (HPMC) can be efficiently prepared by hydrogenating 4-hydroxyacetophenone (4-HAP) under certain conditions. Specifically, it has been found that 4-HAP can be heated under suitable hydrogenation conditions of temperature and pressure in the presence of a suitable palladium catalyst and for a sufficient period of time to form HPMC in relatively high yields. The heating is conducted at a temperature of at least about 20° C., preferably from about 20° C. to about 100° C., in the presence of at least a stoichiometric amount of hydrogen and a catalyst selected from the group consisting of Pd/C; $Pd/Al_2O_3$; $Pd/SiO_2$; and $Pd/CaCO_3$.

In a preferred embodiment, the reaction is conducted until a substantial completion of hydrogenation is indicated by a lack of $H_2$ uptake, normally about one to twelve hours.

In a preferred embodiment, when Pd/C is used, the reaction proceeds at a pressure of from about 14.7 psig to about 5,000 psig, more preferably at a pressure of from about 50 psig to about 500 psig, and most preferably at a pressure of from about 100 psig to about 400 psig.

The hydrogenation conditions also include the use of a suitable solvent/diluent. Diluents/solvents which can be used in the present invention include: (a) water; (b) hydrocarbons such as benzene, toluene, xylene, and low-boiling point petroleum fractions; (c) inorganic gases such as carbon monoxide, carbon dioxide, nitrogen, helium, and argon; (d) dipolar aprotic solvents; and (e) mixtures thereof. The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide, hexamethylphosphoric acid triamide (HMPT), and n-methyl pyrrolidone (NMP). Solvents such as ethanol, methanol, or tetrahydrofuran (THF) may be used in combination with the preceding solvents/diluents. Water, ethanol, methanol, benzene, and toluene (and mixtures thereof) are preferred diluents. The diluents are used in an amount of 2 to 200 mols, preferably 3 to 20 mols per mol of 4-HAP. It is to be understood that any diluent may be used under any temperature and reaction conditions so long as the polymerization of 4-HAP is effected smoothly.

The amount of catalyst employed is that which is catalytically effective in promoting the reaction. Usually, this amount is from about 0.001 weight percent to about 10.0 weight percent based on the weight of the starting material, i.e. 4-HAP.

The length of time which this heating/hydrogenation (reaction) step is conducted is not critical and the only requirement is that the heating be conducted for a period sufficient to form HPMC. Generally, this period is at least five minutes and may be as long as 25 hours, generally from about one to about twelve hours.

After the hydrogenation of 4-HAP, the end product (HPMC) is recovered from the reaction product and the residual fraction containing any unreacted 4-HAP can be recycled as the starting material for the next cycle of hydrogenation. The end product (HPMC) may be recovered from the reaction product by any method. One example is to recover the HPMC as a polymerized product, i.e. the reaction product is first subjected to a decomposition and a polymerization step to polymerize the HPMC to the resulting polymer-polyhydroxystyrene (PHS).

The following specific example is supplied for the purpose of better illustrating the invention. This example is not intended, however, to limit or restrict the scope of the invention in any way and should not be construed as providing conditions, parameters, or values which must be utilized exclusively in order to practice the present invention.

EXAMPLE I

Hydrogenation of 4-Hydroxyacetophenone

4-Hydroxyacetophenone (13.6 g, 0.1 mol) was charged in a 500 ml Zipper autoclave reactor, absolute alcohol (100 ml), and 5% Pd/C (Johnson Matthey's 21R) (1.2 g) was added. The autoclave was first checked for leaks with 100 psig of nitrogen. The autoclave was later pressurized to 300 psig with hydrogen and stirred at 35° C. for three hours. During this time, 0.095 mole of hydrogen was consumed (95% of the theoretical value). The reaction was vented and the contents filtered through a millipore filter yielding a colorless solution. Concentration of this solution in vacuo gave a solid. Traces of ethanol were removed via azeotropic distillation with toluene to afford a white solid (13.8 g). Liquid chromatographic analysis of the product showed 1,4-HPE (or HPMC) (99.0%), 4-HAP (0.2%), and 4-EP (ethyl phenol) (0.8%). $^1$H NMR spectrum of the product showed it to be mainly 1,4-HPE, with traces of 4-HAP.

EXAMPLES II–XII

Using the same procedure set forth in Example I, Examples II–XII were carried out using different reaction conditions as outlined in Table 1. The results are shown in Table 1.

TABLE 1

| | ANALYTICAL | | | | REACTION CONDITIONS | | | | |
|---|---|---|---|---|---|---|---|---|---|
| | | | | | | CATALYST | | | |
| Example No. | ex. std HPMC | 4-HAP | HSM | EP | RUN TIME | 4-HAP (g.) | TYPE & AMOUNT | SOLVENT/ AMOUNT | $H_2$ ADDED | COMMENTS |
| II | 84.79 | 11.08 | 0.00 | 0.37 | 1.6 HRS | 12.0 | 0.6 g. 5% Pd/C | 48 g. MeOH | 227 | 45° C., white crystals |
| III | 74.11 | 0.33 | 0.00 | 16.00 | 1.1 HRS | 18.0 | 1.3 g. 5% Pd/C | 42 g. MeOH | 323 | 55° C., white crystals |
| IV | 83.33 | 0.00 | 0.00 | 10.60 | 3.2 HRS | 6.0 | 0.2 g. 5% Pd/C | 54 g. MeOH | 108 | 35° C., white crystals |
| V | 35.97 | 48.96 | 5.97 | 2.46 | 2.0 HRS | 6.9 | 0.6 g. 5% Pd/C | 51 g. EtOH | 270 | 35° C., RXN PSI 300, white crystal |
| VI | 47.30 | 41.48 | 5.22 | 2.64 | 1.0 HRS | 6.0 | 0.6 g. 5% Pd/C | 51 g. EtOH | **** | 35° C., RXN PSI 300, white crystal |
| VII | 79.95 | 0.00 | 0.00 | 16.57 | 3.0 HRS | 6.0 | 0.6 g. 5% Pd/C | 50 g. MeOH | **** | 35° C., RXN PSI 300, white crystal |
| VIII | | | | | 2.5 HRS | 6.0 | 0.6 g. 5% Pd/C | 45.5 g. MeOH/ 5.6 g. $H_2O$ | 740 | 81° C., RXN PSI 300, liquid after rotovap |
| IX | 86.90 | 0.00 | *** | 10.11 | 2.0 HRS | 8.0 | 0.4 g. 5% Pd/C | 53.4 g. MeOH | 780 | 35° C., RXN PSI 300, white crystal |
| X | 81.36 | 0.86 | *** | 3.55 | 2.0 HRS | 8.0 | 0.2 g. 5% Pd/C | 53.4 g. MeOH | 530 | 35° C., RXN PSI 300, white crystal |
| XI | 28.52 | 69.22 | *** | 2.26 | 4.0 HRS | 20.0 | 1.0 g. 5% Pd/C | 40 g. MeOH | 390 | 35° C., RXN PSI 300, white crystal |
| XII | | | | | 4.5 HRS | 20.0 | 1.0 g. 5% Pd/C | 39.9 g. MeOH | 1140 | 35° C., RXN PSI 300, white crystal |

While the above has been described using 4-hydroxyacetophenone (4-HAP) as the starting material, it is also within the scope of the present invention to use (1) other hydroxyacetophenones (wherein the hydroxy substituents are positioned at different locations on the phenyl ring), and (2) substituted hydroxyacetophenones wherein the remaining four hydrogen atoms (on the phenyl ring) are selectively replaced by an R group, said R being selected from the group consisting of (a) $C_1$–$C_8$ alkyl; (b) $C_6H_5$; (c) halogen (F, Cl, Br, I); (d) hydroxy; and (e) OR where R is the same as defined above. These hydroxyacetophenones and substituted hydroxyacetophenones are all suitable starting materials for use in the present invention process.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing 4-hydroxyphenylmethylcarbinol which comprises the step of heating 4-hydroxyacetophenone in the presence of hydrogen and a catalyst selected from the group consisting of Pd/C, Pd/Al$_2$O$_3$, Pd/SiO$_2$, and Pd/CaCO$_3$ at a temperature of at least about 20° C. for a sufficient period of time to form said carbinol.

2. The process as set forth in claim 1 wherein the hydrogen used is at least a stoichiometric amount.

3. The process as set forth in claim 1 wherein the reaction takes place in the presence of an organic solvent.

4. The process as set forth in claim 1 wherein the reaction takes place in the presence of water.

5. The process as set forth in claim 1 wherein the temperature is from about 20° C. to about 100° C.

6. A process for preparing a carbinol which comprises the step of heating hydroxyacetophenone in the presence of hydrogen and a catalyst selected from the group consisting of Pd/C, Pd/Al$_2$O$_3$, Pd/SiO$_2$, and Pd/CaCO$_3$ at a temperature of at least about 20° C. for a sufficient period of time to form said carbinol.

7. A process for preparing a carbinol which comprises the step of heating a substituted hydroxyacetophenone in the presence of hydrogen and a catalyst selected from the group consisting of Pd/C, Pd/Al$_2$O$_3$, Pd/SiO$_2$, and Pd/CaCO$_3$ at a temperature of at least about 20° C. for a sufficient period of time to form said carbinol.

8. The process as set forth in claim 6 wherein the temperature is less than about 100° C. and the heating step is conducted in the presence of an aprotic polar solvent.

9. The process as set forth in claim 7 wherein the temperature is less than about 100° C.; the heating step is conducted in the presence of an aprotic polar solvent; and the formed carbinol is 4-hydroxyphenylmethylcarbinol.

10. The process as set forth in claim 1 wherein the catalyst is Pd/C.

11. The process as set forth in claim 6 wherein the catalyst is Pd/C.

12. The process as set forth in claim 1 wherein the catalyst is Pd/SiO$_2$.

* * * * *